United States Patent [19]
Machida

[11] Patent Number: 5,285,787
[45] Date of Patent: Feb. 15, 1994

[54] APPARATUS FOR CALCULATING COORDINATE DATA OF DESIRED POINT IN SUBJECT TO BE EXAMINED

[75] Inventor: Yoshio Machida, Tochigi, Japan
[73] Assignee: Kabushiki Kaisha Toshiba, Japan
[21] Appl. No.: 953,760
[22] Filed: Sep. 29, 1992

Related U.S. Application Data

[63] Continuation of Ser. No. 580,762, Sep. 11, 1990, abandoned.

[30] Foreign Application Priority Data

Sep. 12, 1989 [JP] Japan ............... 1-236489

[51] Int. Cl.$^5$ ............... A61B 5/055
[52] U.S. Cl. ............... 128/653.2; 606/130
[58] Field of Search ............... 128/653.1, 653.2, 653.5; 606/130; 378/205

[56] References Cited

U.S. PATENT DOCUMENTS

| | | | |
|---|---|---|---|
| 4,228,799 | 10/1980 | Anichkov et al. | 606/130 |
| 4,644,276 | 2/1987 | Sierocuk et al. | |
| 4,923,459 | 5/1990 | Nambu | 606/130 |
| 5,005,578 | 4/1991 | Greer et al. | 128/653.2 |

FOREIGN PATENT DOCUMENTS

| | | |
|---|---|---|
| 3831278 | 3/1989 | Fed. Rep. of Germany . |
| 2164856 | 4/1986 | United Kingdom . |
| 8800340 | 1/1988 | World Int. Prop. O. . |

*Primary Examiner*—Ruth S. Smith
*Attorney, Agent, or Firm*—Limbach & Limbach

[57] ABSTRACT

A method of calculating coordinate data of a desired point in a subject to be examined is disclosed. A phantom image is obtained by integrally photographing a second frame, a frame coordinate phantom, and a second indicator phantom by using a computed tomographic apparatus. A subject image is then obtained by integrally photographing a first frame, the subject, and a first indicator phantom at the same position assumed when the phantom image is photographed. Coordinate data is obtained by correcting the deviation between the coordinates of the subject on the real space and the coordinates of the subject on the image photographed by the computed tomographic apparatus.

8 Claims, 14 Drawing Sheets

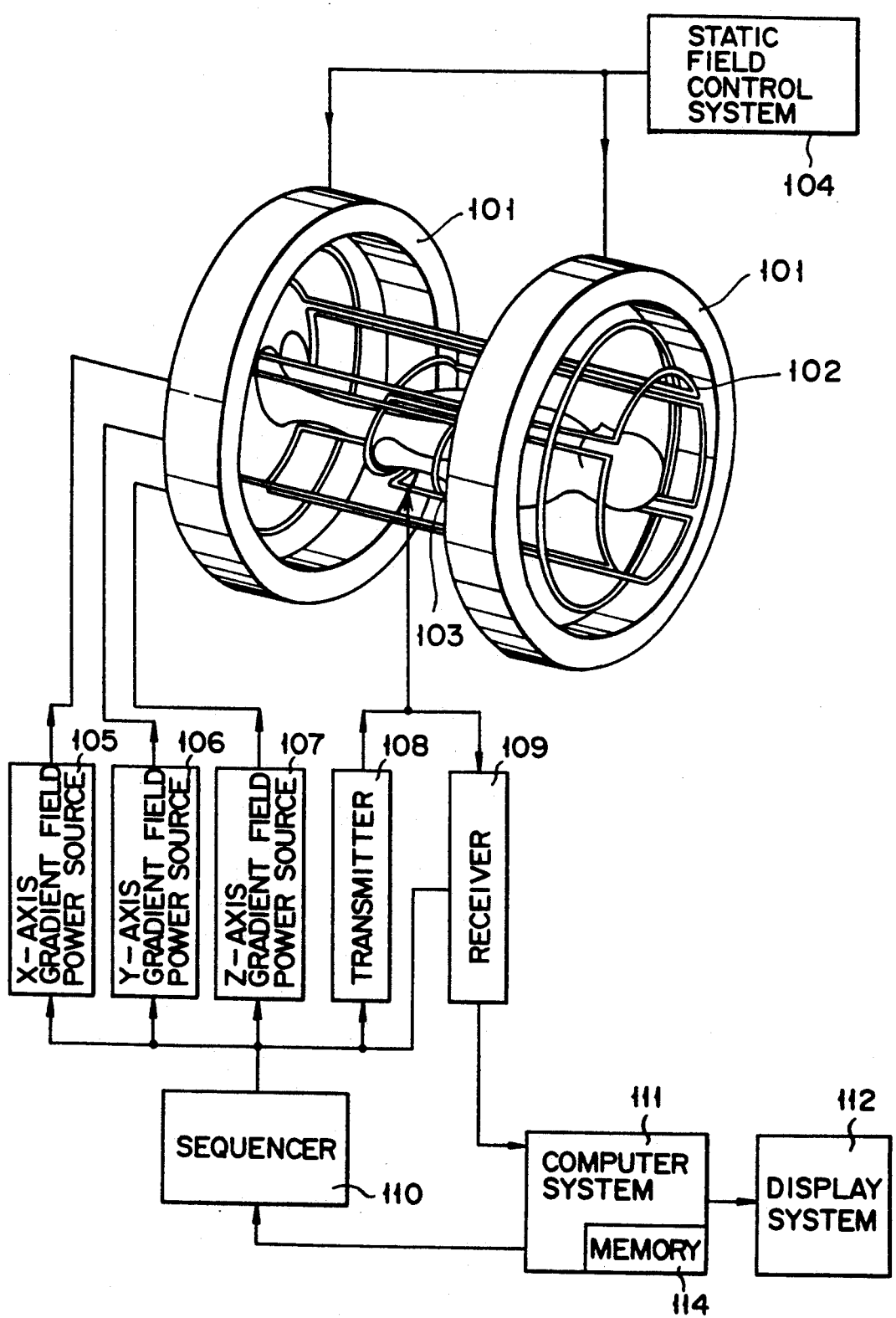
F I G. 3

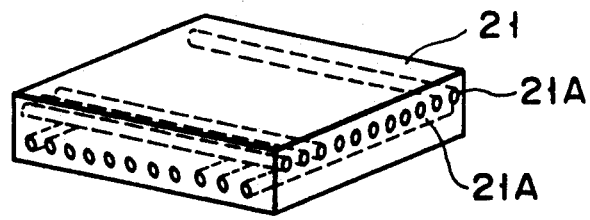
F I G. 10
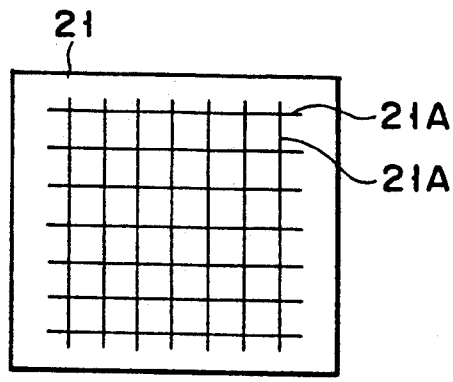
F I G. 11
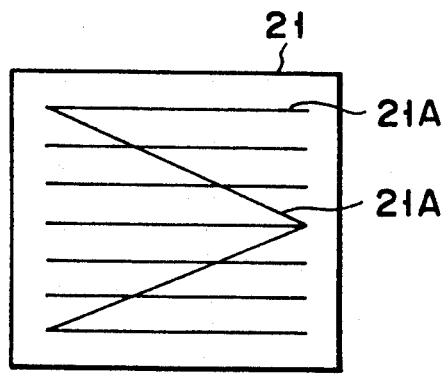
F I G. 12
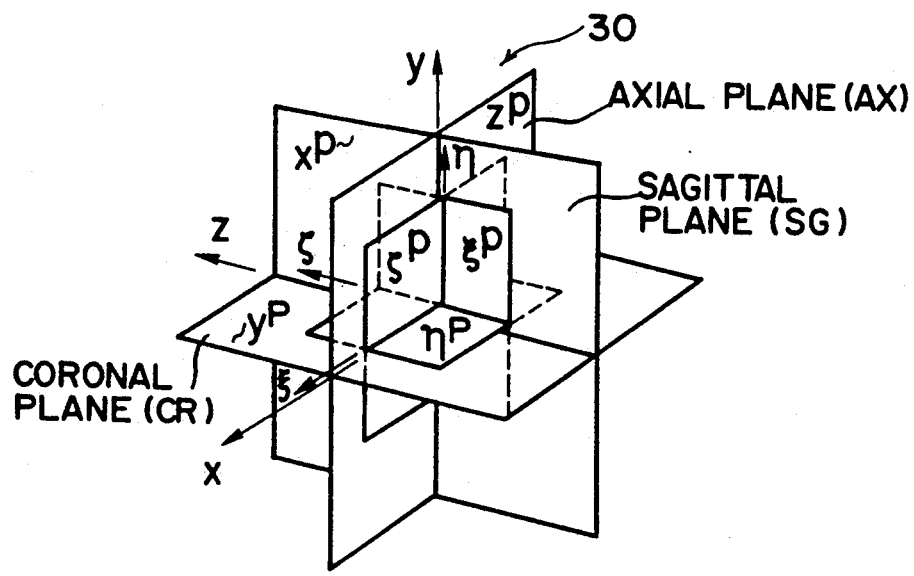
F I G. 13

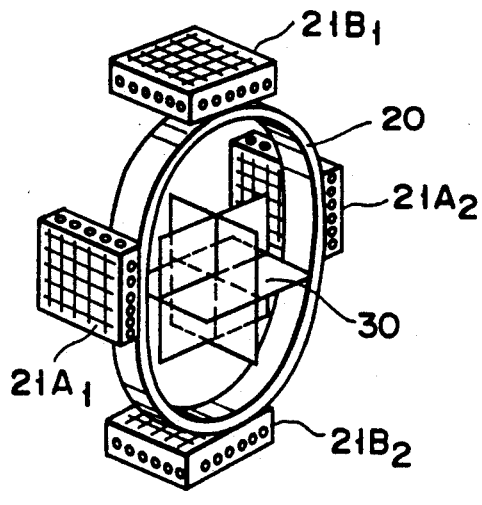
F I G. 14A
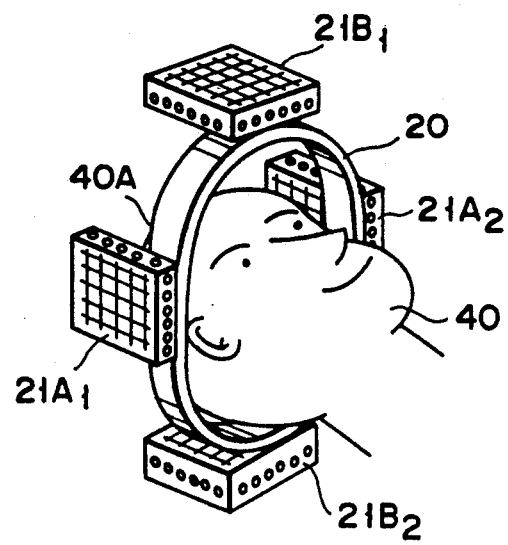
F I G. 14B
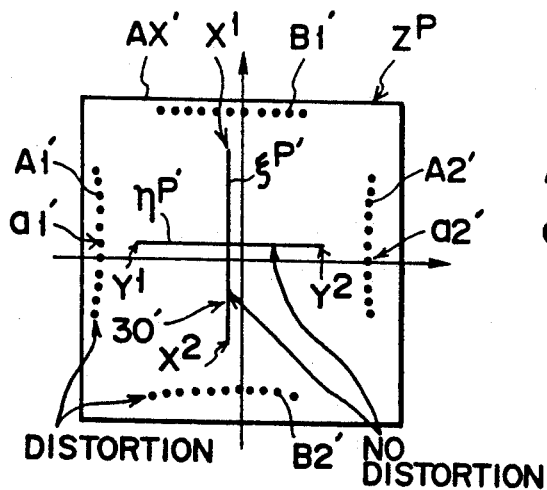
F I G. 15A
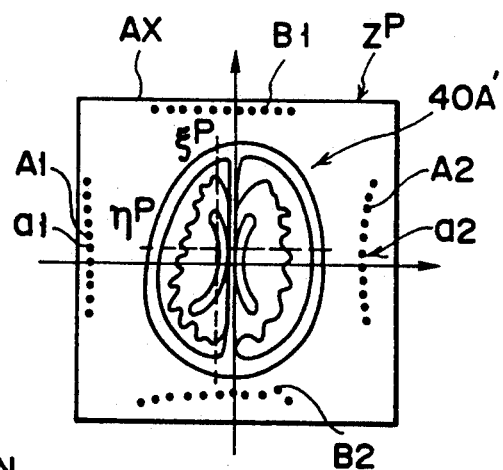
F I G. 15B

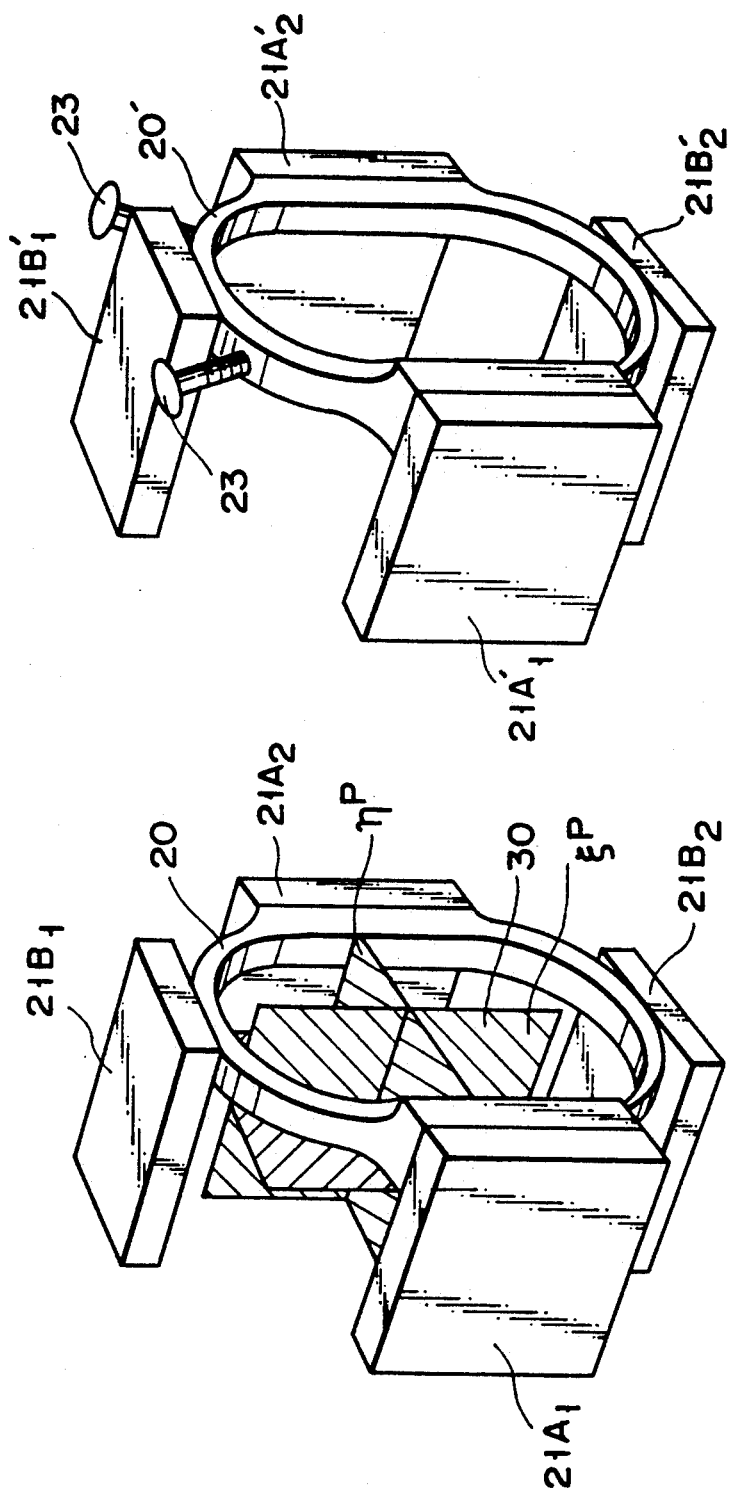

APPARATUS FOR CALCULATING COORDINATE DATA OF DESIRED POINT IN SUBJECT TO BE EXAMINED

This is a continuation of co-pending application Ser. No. 07/580,762 filed on Sep. 11, 1990, now abandoned.

BACKGROUND OF THE INVENTION

1. Field of the Invention

The present invention relates to an apparatus for calculating coordinate data of a desired point in a subject to be examined which is required when stereotaxy (stereotactic surgery) or the like is to be performed by using a computed tomographic apparatus such as an MRI apparatus (Magnetic Resonance Imaging Apparatus), and a method of calculating coordinate data of a desired point in a subject to be examined by using the same.

2. Description of the Related Art

Coordinate data of a desired point in a subject to be examined is used, for example, for stereotaxy surgery as one of operations of neurosurgeon. In stereotaxy, the position of a morbid portion in the brain of a patient is identified with the aid of an image, and an operation is performed, e.g., inserting a biopsy cannula in the identified portion so as to remove the morbid portion. As the image, an X-ray image (Roentgen image) obtained by an X-ray diagnosing apparatus has been used. Recently, however, CT stereotaxy using an X-ray CT apparatus as a computed tomographic apparatus and MRI stereotaxy using an MRI apparatus as a computed tomographic apparatus have been performed.

MRI stereotaxy is conventionally realized by the coordinate calculation step of calculating the coordinate value of a morbid portion in a subject to be examined, and the step of operating a stereotactic apparatus on the basis of the calculated coordinate value, i.e., the operation step. FIG. 1 shows an apparatus used in the coordinate calculation step and a subject to be examined. FIG. 2 shows an apparatus used in the operation step, i.e., a stereotactic apparatus and the subject.

As shown in FIG. 1, in the apparatus used in the coordinate calculation step, a head portion 40A of a subject 40 to be examined is held in an annular frame 20. In this case, an indicator phantom 21 is mounted on the frame 20 in order to indicate X-, Y-, and Z-coordinates. The frame 20 is placed at a predetermined position in a photographable region of a computed tomographic apparatus (not shown) while the head portion 40A is held by the frame 20, and a photographing operation is performed to obtain, e.g., an axial plane image. By observing this image, the position of the morbid portion appearing on the image is recognized and identified with X-, Y-, and Z-coordinates by referring to the indicator phantom 21. The indicator phantom 21 is detached from the frame 20, and a stereotactic apparatus 22 is mounted. Thereafter, for example, a biopsy cannula 22A of the apparatus 22 is pierced into the head portion 40A to reach the position coordinates of the morbid portion obtained in the above described step as a target, and the morbid portion is removed.

In the execution of the above-described stereotaxy, since a surgical operation is to be performed for a brain, high positional precision is required in identification of a morbid portion.

In an MRI apparatus, however, because of the characteristics of static and gradient fields, field distortion is abruptly increased with an increase in distance from the field center, and following this field distortion, image distortion is abruptly increased. Example, image distortion corresponding to 5 mm may be caused at a position near the frame, thus posing a problem in execution of stereotaxy requiring high positional precision.

SUMMARY OF THE INVENTION

It is, therefore, an object of the present invention to provide an apparatus for calculating coordinate data of a desired point in a subject to be examined and a method of calculating coordinate data of a desired point in a subject to be examined by using the same, more particularly, an apparatus and method capable of obtaining high-precision coordinate data.

In order to achieve the above object, according to the present invention, there is provided (1) an apparatus for calculating coordinate data of a desired point in a subject to be examined, comprising:

a frame which has a shape capable of detachably holding the subject therein and can be arranged in a photographable region in a gantry of a computed tomographic apparatus; and a frame coordinate phantom which is detachably arranged inside the frame in place of the subject, has a coordinate display member capable of displaying coordinates of at least one axis of X-, Y-, and Z-coordinates, and can be photographed by the computed tomographic apparatus.

In order to achieve the above object, according to the present invention, there is provided another apparatus for calculating coordinate data of a desired point in a subject to be examined, comprising:

a first frame which has a shape capable of holding the subject therein and can be arranged in a photographable region in a gantry of a computed tomographic apparatus;

a second frame having geometrically the same shape as that of the first frame; and a frame coordinate phantom which is fixed inside the second frame, has a coordinate display member capable of displaying coordinates of at least one axis of X-, Y-, and Z-coordinates of, and can be photographed by the computed tomographic apparatus.

In order to achieve the above object, according to the present invention, there is provided still another apparatus for calculating coordinate data of a desired point in a subject to be examined, comprising:

a frame which has a shape capable of detachably holding the subject therein and can be arranged in a photographable region in a gantry of a computed tomographic apparatus;

an indicator phantom which is fixed to an outer surface of the frame, has a coordinate display member capable of displaying coordinates of at least one axis of X-, Y-, and Z-coordinates, and can be photographed by the computed tomographic apparatus; and a frame coordinate phantom which is detachably arranged inside the frame in place of the subject, has a coordinate display member capable of displaying coordinates of at least one axis of X-, Y-, and Z-coordinates, and can be photographed by the computed tomographic apparatus.

In order to achieve the object, according to the present invention, there is provided still another apparatus for calculating coordinate data of a desired point in a subject to be examined, comprising:

a first frame which has a shape capable of holding the subject therein and can be arranged in a photographable region in a gantry of a computed tomographic apparatus;

a first indicator phantom which is fixed to an outer surface of the first frame, has a coordinate display member capable of displaying coordinates of at least one axis of X-, Y-, and Z-coordinates, and can be photographed by the computed tomographic apparatus;

a second frame having geometrically the same shape as that of the first frame;

a second indicator phantom which is fixed to an outer surface of the second frame, has a coordinate display member capable of displaying coordinates of at least one axis of X-, Y-, and Z-coordinates, and can be photographed by the computed tomographic apparatus; and a frame coordinate phantom which is fixed inside the second frame, has a coordinate display member capable of displaying coordinates of at least one of X-, Y-, and Z-coordinates, and can be photographed by the computed tomographic apparatus.

In order to achieve the object, according to the present invention, there is provided a method of calculating coordinate data of a desired point in a subject to be examined comprising the steps of:

arranging the frame having the frame coordinate phantom mounted thereon in a photographable region in a computed tomographic apparatus, and integrally photographing the frame and the frame coordinate phantom, thereby obtaining a phantom image;

arranging the frame holding the subject in place of the frame coordinate phantom therein at the same position as that assumed when the phantom image is photographed, and integrally photographing the frame and the subject, thereby obtaining a subject image;

obtaining a positional relationship on an image between the frame coordinate phantom and the subject and a positional relationship between the frame and the subject on a real space on the basis of a correlation between the phantom image and the subject image; and obtaining coordinate data by correcting a deviation between coordinates of the subject on the real space and coordinates of the subject on the image photographed by the computed tomographic apparatus in relation to the desired point in the subject on the basis of the positional relationships on the image and the real space.

In order to achieve the object, according to the present invention, there is provided another method of calculating coordinate data of a desired point in a subject to be examined comprising the steps of:

arranging the second frame having the frame coordinate phantom fixed thereto in a photographable region in a computed tomographic apparatus, and integrally photographing the second frame and the frame coordinate phantom, thereby obtaining a phantom image;

arranging the first frame holding the subject therein at the same position as that assumed when the phantom image is photographed, and integrally photographing the first frame and the subject, thereby obtaining a subject image;

obtaining a positional relationship between the frame coordinate phantom and the subject on an image and a positional relationship between the first and second frames and the subject on a real space on the basis of a correlation between the phantom image and the subject image; and obtaining coordinate data by correcting a deviation between coordinates of the subject on the real space and coordinates of the subject on the image photographed by the computed tomographic apparatus in relation to the desired point in the subject on the basis of the positional relationships on the image and the real space.

In order to achieve the object, according to the present invention, there is provided still another method of calculating coordinate data of a desired point in a subject to be examined comprising the steps of:

arranging the frame having the frame coordinate phantom mounted on an inner surface thereof therein and the indicator phantom fixed on an outer surface thereof in a photographable region in a computed tomographic apparatus, and integrally photographing the frame, the frame coordinate phantom, and the indicator phantom, thereby obtaining a phantom image;

arranging the frame holding the subject in place of the frame coordinate phantom therein at the same position as that assumed when the phantom image is photographed, and integrally photographing the frame, the subject, and the indicator phantom, thereby obtaining a subject image;

obtaining a positional relationship between the frame coordinate phantom and the subject on an image and a positional relationship between the frame and the subject on a real space on the basis of a correlation between the indicator phantom on the phantom image and the indicator phantom on the subject image; and obtaining coordinate data by correcting a deviation between coordinates of the subject on the real space and coordinates of the subject on the image photographed by the computed tomographic apparatus in relation to the desired point in the subject on the basis of the positional relationships on the image and the real space.

In order to achieve the object, according to the present invention, there is provided still another method of calculating coordinate data of a desired point in a subject to be examined comprising the steps of:

arranging the second frame having the frame coordinate phantom fixed to an inner surface thereof and the second indicator phantom fixed on an outer surface thereof in a photographable region in a computed tomographic apparatus, and integrally photographing the second frame, the frame coordinate phantom, and the second indicator phantom, thereby obtaining a phantom image;

arranging the first frame holding the subject therein and having the first indicator phantom fixed to an outer surface thereof at the same position as that assumed when the phantom image is photographed, and integrally photographing the first frame, the subject, and the first indicator phantom, thereby obtaining a subject image;

obtaining a positional relationship between the frame coordinate phantom and the subject on an image and a positional relationship between the first and second frames and the subject on a real space on the basis of a correlation between the second indicator phantom on the phantom image and the first indicator phantom on the subject image; and obtaining coordinate data by correcting a deviation between coordinates of the subject on the real space and coordinates of the subject on the image photographed by the computed tomographic apparatus in relation to the desired point in the subject on the basis of the positional relationships on the image and the real space.

In addition, since almost no image distortion is present inside the frame placed in the photographable region in the computed tomographic apparatus, a frame coordinate phantom image appearing on a phantom image represents the positional coordinates of the frame. Therefore, a correct position of the frame itself and a correct positional relationship between the frame and a subject to be examined can be obtained on the basis of the phantom image and a subject image photographed at the same position as that assumed when the phantom image is photographed. With this, calibration data for calibrating the deviation between the coordinates of the subject on the real space and the coordinates of the subject on the image photographed by the computed tomographic apparatus can be obtained. Moreover, since both the images are obtained at the frame having the indicator phantom mounted on the outer surface thereof, a more correct positional relationship of the frame between the images can be obtained.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 3 is a view showing an overall arrangement of an MRI apparatus used in the present invention;

FIGS. 4 to 8 show problems based on the field characteristics of the MRI apparatus, in which FIG. 4 is a graph showing static field distortion characteristics, FIG. 5 is a graph showing gradient field distortion characteristics, FIG. 6 is a graph showing distortion characteristics based on static and gradient fields, FIG. 7 is a graph showing image distortion appearing when static field distortion is present, and FIG. 8 is a graph showing image distortion appearing when gradient field distortion is present;

FIGS. 9A and 9B show a coordinate calculation apparatus according to the first embodiment of the present invention, which includes indicator phantoms and a detachable frame coordinate phantom, in which FIG. 9A is a perspective view showing a state wherein phantom images are to be photographed, and FIG. 9B is a perspective view showing a state wherein a subject image is to be photographed;
a
FIG. 10 is a perspective view showing an indicator phantom as an example;

FIG. 11 is a plan view showing an indicator phantom as another example;

FIG. 12 is a plan view showing an indicator phantom as still another example;

FIG. 13 is a perspective view showing a MRI apparatus coordinate system and a frame (the coordinate calculation apparatus) coordinate system as an example;

FIG. 14A is a perspective view showing a state wherein phantom images are to be photographed by using the coordinate calculation apparatus in FIG. 9A;

FIG. 14B is a perspective view showing a state wherein a subject image is to be photographed by using the coordinate calculation apparatus in FIG. 9B;

FIG. 15A is a view showing phantom images on an axial plane by using the apparatus in FIG. 14A;

FIG. 15B is a view showing a subject image on an axial plane by using the apparatus in FIG. 14A;

FIGS. 23A and 23B show a coordinate calculation apparatus according to the second embodiment of the present invention, which includes indicator phantoms and a fixed type frame coordinate phantom, in which FIG. 23A is a perspective view showing a state wherein phantom images are to be photographed, and FIG. 23B is a perspective view showing a state wherein a subject image is to be photographed;

FIGS. 24A and 24B show a coordinate calculation apparatus according to the third embodiment of the present invention, which does not include any indicator phantom but includes a detachable frame coordinate phantom, in which FIG. 24A is a perspective view showing a state wherein phantom images are to be photographed, and FIG. 24B is a perspective view showing a state wherein a subject image is to be photographed;

FIGS. 25A and 25B show a coordinate calculation apparatus according to the fourth embodiment of the present invention, which does not include any indicator phantom but includes a fixed type frame coordinate phantom, in which FIG. 25A is a perspective view showing a state wherein phantom images are to be photographed, and FIG. 25B is a perspective view showing a state wherein a subject image is to be photographed;

DETAILED DESCRIPTION OF THE PREFERRED EMBODIMENTS

Figure 1:
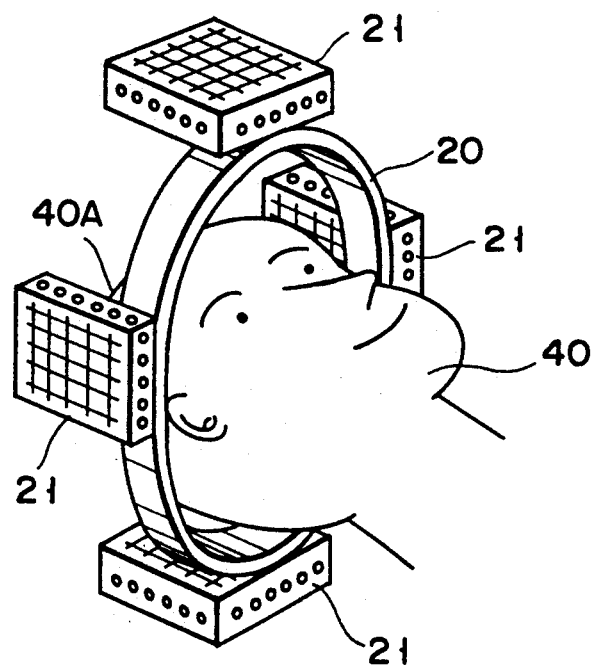
FIG. 1 is a perspective view showing a conventional coordinate calculation apparatus constituted by a frame and indicator phantoms in relation to a subject to be examined.

An MRI apparatus will be described below.

An MR phenomenon is a phenomenon in which an atomic nucleus having a non-zero spin and a magnetic moment and placed in a static field resonantly absorbs/radiates an electromagnetic wave having a specific frequency. The atomic nucleus resonates at an angular frequency $\omega_O$ ($\omega_O = 2\pi\gamma_O$, $\gamma_O$; Larmor frequency) given by the following equation:

$$\omega_O \gamma H_O$$

where $\gamma$ is the gyromagnetic ratio unique to the type of atomic nucleus, and $H_O$ is the static field intensity.

The apparatus for diagnosing a living body by using the above-mentioned principle is designed to obtain diagnosis data reflecting an atomic nucleus density, a longitudinal relaxation time $T_1$, a transverse relaxation time $T_2$, a flow, a chemical shift, and the like, e.g., a slice image of a subject to be examined in a nondestructive manner by performing signal processing of an electromagnetic wave having the same frequency as described above which is excited upon the above-mentioned resonance absorption.

In acquisition of diagnosis data by MR, the entire portion of the subject placed in the static field can be excited and signals therefrom can be acquired. In practice, however, an MRI apparatus is designed to excite a specific portion and acquire signals therefrom due to limitations on the apparatus arrangement and clinical requirements in terms of imaging.

In this case, a specific portion as an imaging target is generally a slice portion having a certain thickness. Echo signals or MR signals of FID signals from this slice portion are acquired by executing a data encode procedure a large number of times. The acquired data group is then subjected to image reconstruction processing by a two-dimensional Fourier transform method, thus generating an image of the specific slice portion.

FIG. 3 shows an overall arrangement of an MRI apparatus used in the present invention. As shown in FIG. 3, a magnet assembly which can accommodate a subject 40 to be examined includes static coils 101 of a normal conduction or superconduction scheme (may be constituted by permanent magnets) 101, X-, Y-, and Z-axis gradient field generating coils 102 for generating gradient fields to provide position data of an excited portion to an MR signal, and a probe 103 constituted by a transmission/reception system, e.g., transmission and reception coils, for transmitting a rotating high-frequency field and detecting excited MR signals (echo signals and FID signals).

If the superconduction scheme is employed, the apparatus includes a supply control system for a coolant and is mainly constituted by a static field control system 104 for ON/OFF-controlling a static field power source, a transmitter 108 for performing transmission control of RF pulses, a receiver 109 for performing reception control of excited MR signals, X-, Y-, and Z-axis gradient field power sources 105, 106, and 107 for performing excitation control of the X-, Y-, and Z-axis gradient field generating coils 102, a sequencer 110 for executing a pulse sequence for data acquisition, a computer system 111 for controlling the respective components and performing signal processing of a detection signal, and a display unit 112 for displaying an image based on the processed signal. In addition, the computer system 111 includes a memory 114 for storing a phantom image (to be described later).

In the pulse sequence for data acquisition, the transmitter 108 is driven to apply an RF pulse of a rotating field from the probe 103 to the subject 40. At the same time, the gradient field sources 105, 106, and 107 are driven to apply gradient fields $G_X$, $G_Y$, and $G_Z$ as a slice gradient field ($G_S$), a phase encode gradient field ($G_E$), and a read gradient field ($G_R$), respectively, from the gradient field generating coils 102 to the subject 40. With this operation, a signal from a specific portion is acquired by the probe 103. A data group is obtained by repeatedly executing this sequence a predetermined number of times, and an image is generated from this data group.

An MRI apparatus of this type which has recently been regarded as a promising apparatus has the following advantages over an X-ray CT apparatus (X-ray computed tomographic apparatus) which is often compared with the former apparatus. In the MRI apparatus, an arbitrary tomographic image of a subject (to be examined) such as an axial plane image, a sagittal plane image, a coronal plane image, an oblique plane image can be obtained by a simple electrical operation.

In addition, a photographed image is diagnosis data reflecting an atomic nucleus density, spin-lattice relaxation times $T_1$ and $T_2$, a flow, a chemical shift, and the like, and hence is expected to be used in a variety of manners in image diagnosis. For example, in the MRI apparatus, the structure of a lower portion of a deep-brain can be imaged without any artifact, and a minute nuclei-nervus can also be imaged.

With the above advantages, the use of the MRI apparatus has been studied and effectively practiced in image diagnosis which cannot be appropriately performed by the X-ray CT apparatus, especially in the field of diagnosis of neurosurgeon.

The MRI apparatus as a computed tomographic apparatus, however, has the following characteristics, which pose problems in terms of accuracy of identification, i.e., proper execution of stereotaxy. In the MRI apparatus, static and gradient fields are distorted. For this reason, an actual object (an object on an actual space) does not properly appear on an acquired image in relation to the shape and position of the object.

Figure 4:
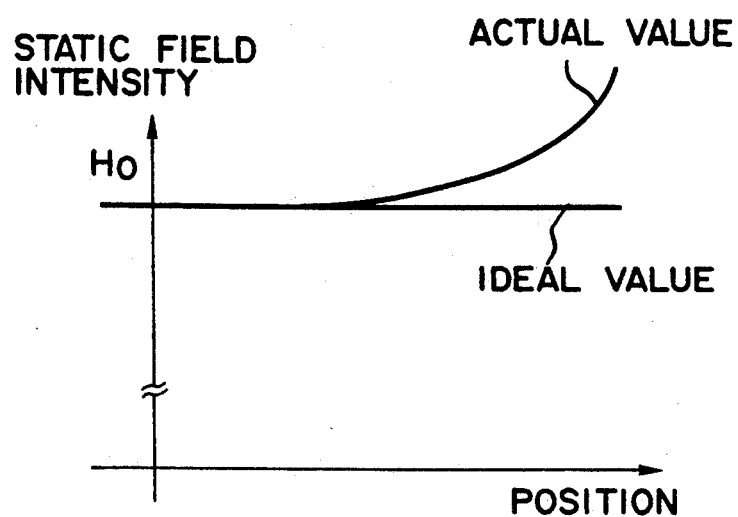
Figure 5:
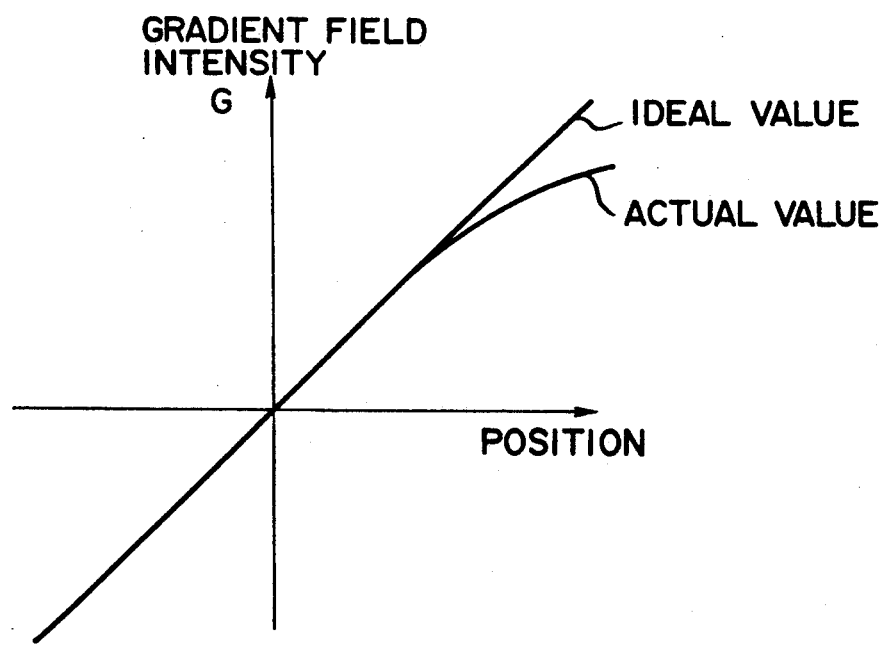
Figure 6:
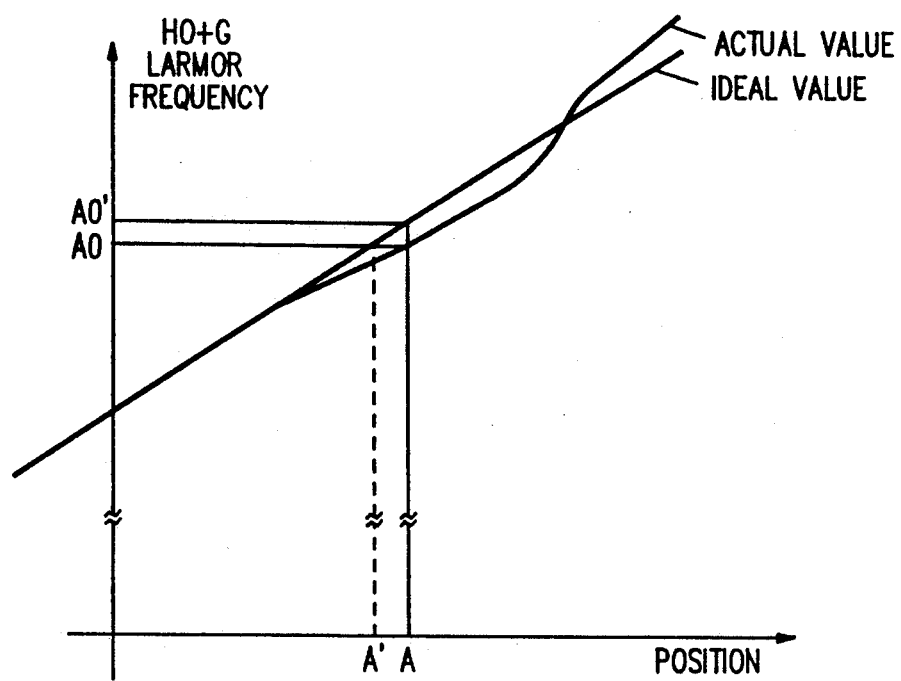

That is, as shown in FIG. 4, the ideal static field intensity $H_O$ is spatially uniform, but an actual intensity is distorted. In addition, as shown in FIG. 5, an ideal gradient field intensity G spatially has linearity, but an actual intensity is distorted. Therefore, an acquired image inevitably includes a positional deviation. As shown in FIG. 6, a gradient field intensity corresponding to static field intensity $H_O$+gradient field intensity G=Larmor frequency ideally exhibits linear characteristics, but is actually distorted.

For this reason, a field intensity at a point A in FIG. 6 is ideally a field intensity $A_O$ but is actually a field intensity $A_O$. In addition, the field intensity $A_O$ should appear at a point A' but actually appears at a different point, which is similar to the presence of a real image A and an actual image A'. Moreover, the distortion of the static field intensity $H_O$ and of the gradient field intensity G is abruptly increased with an increase in distance from the field center, thus posing a problem.

Figure 7:
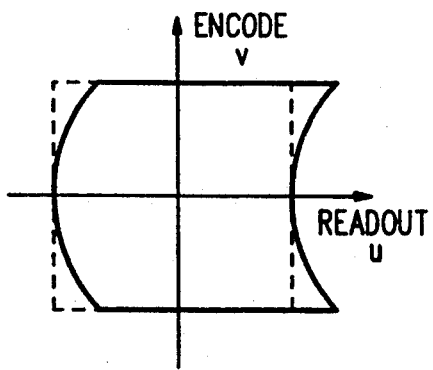

FIG. 7 illustrates a state wherein the static field intensity $H_O$ has nonuniformity. In this case an image of an object indicated by a dotted line (square) is distorted in a direction u of the read gradient field $G_R$.

Figure 8:
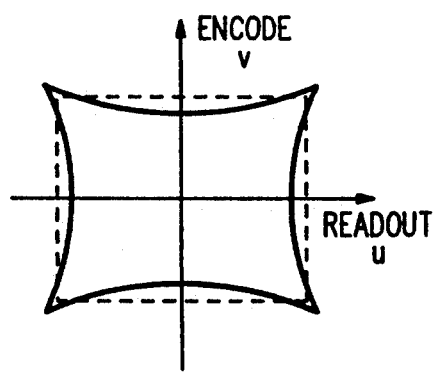

FIG. 8 illustrates a state wherein the gradient field intensity G has nonlinearity. In this case, the image of the object indicated by the dotted line (square) is distorted in the direction u of the read gradient field $G_R$ and a direction u of the encode gradient field $G_E$.

As described above, in the MRI apparatus, distortion is abruptly increased with an increase in distance from the field center because of the characteristics of static and gradient fields. Distortion corresponding to about 5 mm may occur at a position near a frame. This poses a serious problem in the execution of stereotaxy requiring high positional precision.

Under the circumstances, the apparatus and method of the present invention which will be described in detail below are effective.

An embodiment of coordinate calculation according to the present invention will be described below with reference to the accompanying drawings.

Figure 9B:
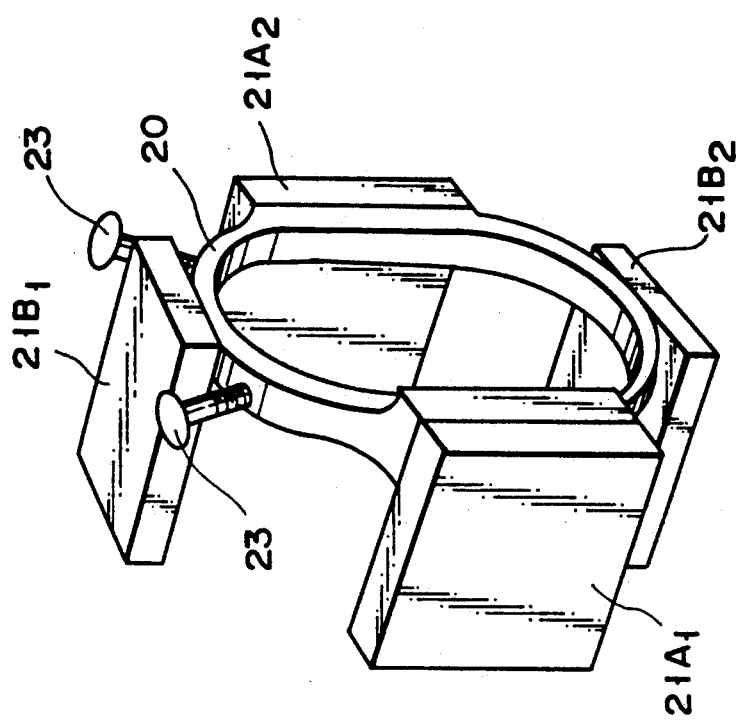
Figure 9A:
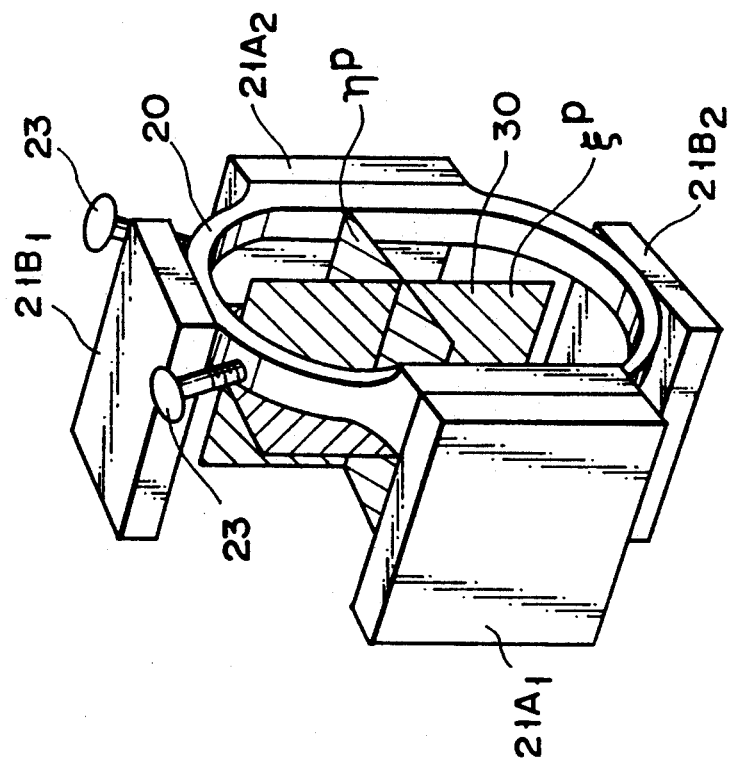

FIGS. 9A and 9B are perspective views showing a stereotaxy frame, an indicator phantom, and a frame coordinate phantom which constitute a main portion of a coordinate calculation apparatus according embodiment of the present invention.

As shown in FIG. 9A, a stereotaxy frame 20 can be arranged in a photographable region in the gantry of an MRI apparatus (not shown) and is designed to hold a head portion 40A of a subject 40 inside its annular frame. The frame 20 includes a plurality of screws 23 for fixing the head portion 40A.

In addition, four indicator phantoms 21 (21A1, 21A2, 21B1, and 21B2) each of which can be photographed by the MRI apparatus and has an X-Y-Z coordinate display member are arranged outside the frame 20. These indicator phantoms 21 are detachably mounted on the frame 20.

FIGS. 10 to 12 show examples of the indicator phantom 21. As shown in FIGS. 10 and 11, the indicator phantom 21 may be designed such that a plurality of water pipes 21A are arranged parallel to each other, and a plurality of other water pipes 21A are arranged parallel to each other on the former pipes 21A so as to be perpendicular to each other. Alternatively, as shown in FIG. 12, the indicator phantom 21 may be designed such that a pluralty of water pipes 21A ar arranged parallel to each other, and two other water pipes 21A are obliquely arranged on the former water pipes 21A. With such an arrangement, three-axis orthogonal coordinates can be recognized by an image of the water pipes 21A appearing on an acquired tomographic image.

A frame coordinate phantom 30 is detachably arranged inside the frame 20. This frame coordinate phantom 30 can be photographed by the MRI apparatus and has an X-Y-Z coordinate display member constituted by, e.g., three orthogonal planes. With the above-described arrangement, for example, the stereotactic apparatus 22 shown in FIG. 2 can be mounted on the frame 20 after the indicator phantoms 21 are detached from the frame 20.

A coordinate calculation method using the coordinate calculation apparatus of this embodiment, which has the above-described arrangement, will be described below together with a description of MRI stereotaxy.

The coordinate system will be described first. Assume, as shown in FIG. 13, that the MRI apparatus has the X-Y-Z coordinate system, and the coordinate calculation apparatus (frame 20) has the $\xi$-$\eta$-$\zeta$ coordinate system. With this arrangement, an image for calibration (phantom image) is given by the X-Y-Z coordinate system. In addition, the planes of the frame coordinate system are respectively represented by the $\xi$-$\eta$, $\eta$-$\zeta$ and $\zeta$-$\xi$ planes. In this case, the $\xi$-$\eta$ plane is represented by $\zeta^P$; the $\eta$-$\zeta$ plane, by $\xi^P$; and $\zeta$-$\xi$ plane, by $\eta^P$.

As is shown in FIG. 14A, the indicator phantoms 21 are mounted on the surface of the frame 20. A frame coordinate phantom 30 is located in the frame 20. The frame 20, the indicator phantoms 21, and the frame coordinate phantom 30 constitute an integral unit. Preferably, the phantom 30 is fixed to the frame 20 at the position where the stereotaxy device is attached. This is because the stereotaxy device has a high mechanical precision. The frame 20 is positioned within the gantry of the MRI apparatus, such that the integral unit is placed in the photographable region in the gantry, preferably at the position where the intersection of the phantom 30 is located at the center of the magnetic field. When a slice photographing operation is performed among, e.g., the X-Y plane, a phantom image AX' of an axial plane image or the like o which images (A1', A2', B1', and B2') of the indicator phantoms 21 and an image 30' ($\zeta$P, $\eta$P) of the frame coordinate phantom 30 appear is acquired, as shown in FIG. 15A.

Subsequently, the frame coordinate phantom 30 is detached from the frame 20. As shown in FIG. 14B, the head portion 40A of the subject 40 is held in place of the frame coordinate phantom 30, and the frame 20 which is holding the head portion 40A is fixed to the same position as that assumed when the phantom image is photographed, which is located in the photographable region of the MRI apparatus, upon positioning control. Thereafter, similar to the above-described operation of acquiring the phantom image, a slice photographing operation is performed along, e.g., the X-Y plane to acquire, e.g., a subject image AX of an axial plane image on which an image (40A') of the head portion 40A and images (A1, A2, B1, and B2) of the indicator phantoms 21 appear.

These phantom and subject images are used to obtain calibration data for calibrating the deviation between the position (coordinates) of the frame 20 and the position (coordinates) of the head portion 40A on the real space. The subject image is observed to recognize a desired position on the image as a morbid portion, and the coordinates of the recognized position on the real space are calculated by using the calibration data. This calculation method is realized by data processing by means of a computer or the like, which will be described in detail later.

Figure 2:
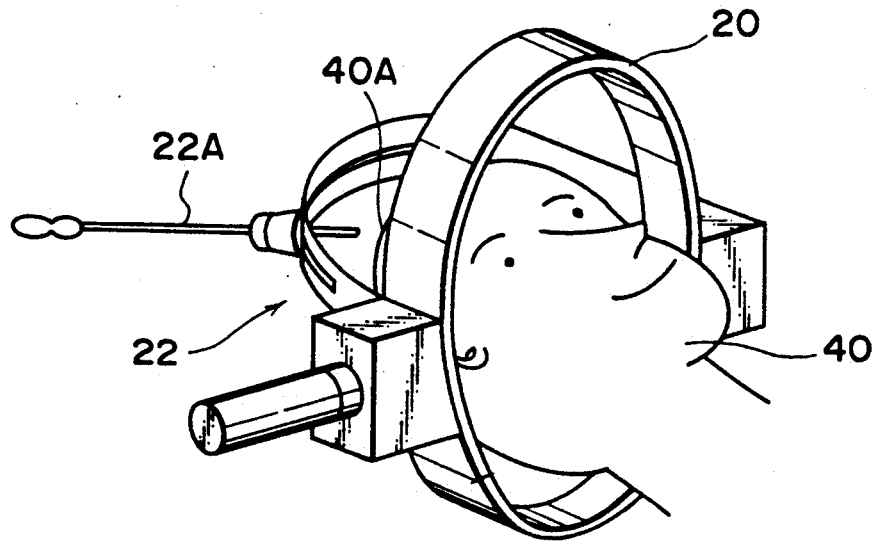
FIG. 2 is a perspective view showing a conventional stereotactic apparatus in relation to a frame and a subject to be examined.

Subsequently, the indicator phantoms 21 are detached from the frame 20, and, for example, the stereotactic apparatus 22 shown in FIG. 2 is mounted on the frame 20 while the head portion 40A is held therein. The biopsy cannula 22A is inserted in the head portion 40A to the position (coordinates) of the morbid portion obtained by the above-mentioned processing as a target so as to remove the morbid portion.

The calculation method of recognizing the deviation between the position (coordinates) of the frame 20 and the position (coordinates) of the head portion 40A on the real space by using the phantom and subject images, i.e., obtaining the calibration data will be described below.

The images (A1', A2', B1', and B2') of the indicator phantoms 21 on the phantom image AX' and the images (A1, A2, B1, and B2) of the indicator phantoms 21 on the subject image AX respectively appear at substantially the same positions. By using this phenomenon, a transformation formula $\phi(\phi_{AX}(AX') \approx AX)$ for causing these images to coincide with each other is obtained.

Since the image 30' of the frame coordinate phantom 30 represents coordinates inside the frame 20, a position (coordinates) on the real space can be obtained on the basis of the transformation formula and the coordinates inside the frame 20.

If, for example, a target point is set on the subject image AX, the coordinates of the target position can be recognized from the image 30' of the frame coordinate phantom image 30. The obtained coordinates are compensated by the transformation formula $\phi$. Therefore, the biopsy cannula 22A can be properly inserted in a portion corresponding to the position data of the head portion 40A on the real space. Note that the transformation formula $\phi$ is calculated by two dimension congruent transformation of superimposing using at least two points of the group of A1', A2', B1', and B2' and the group of A1, A2, B1, and B2.

The calculation of the transformation formula for causing the images (A1', A2', B1', and B2') of the indicator phantoms 21 and the images (A1, A2, B1, and B2) of the indicator phantoms 21 on the subject image AX to coincide with each other is a means for ensuring positional coincidence between the phantom image AX' and the subject image AX. If, for example, high-precision bed date control is performed and satisfactory reproducibility can be obtained in relation to photography positioning, position data may be obtained simply on the basis of the image 30' of the frame coordinate phantom 30 and the image 40A; of the head portion 40 without calculation of the transformation formula $\phi$.

Figure 16:
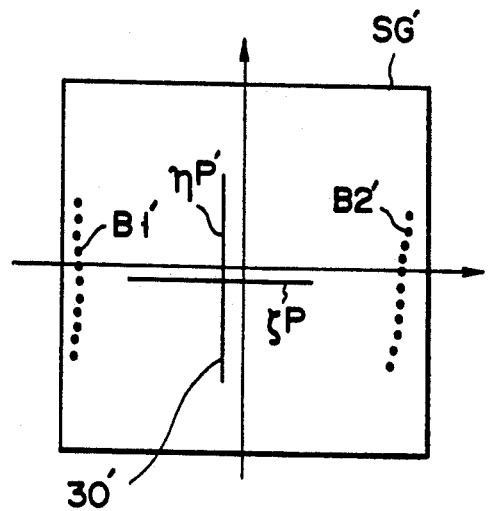
FIGS. 16 and 17 are views showing a case wherein coordinate calibration is performed by applying the present invention to images on sagittal planes.
Figure 17:
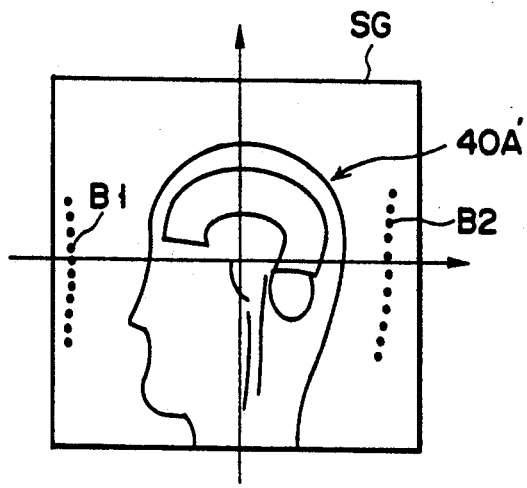
Figure 18:
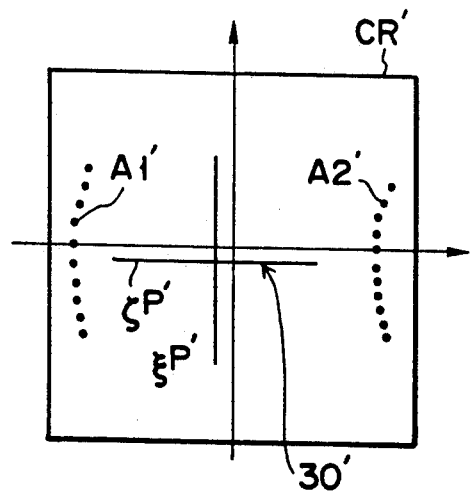
FIGS. 18 and 19 are views showing a case wherein coordinate calibration is performed by applying the present invention to images on coronal planes.
Figure 19:
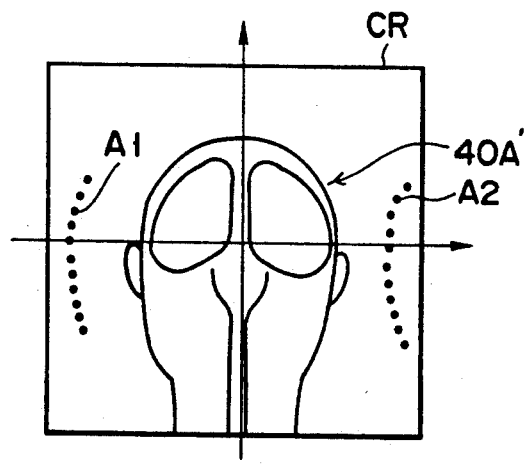

FIGS. 15A and 15B show the case wherein the present invention is applied to images on axial planes. However, the present invention is not limited to this. For example, the present invention can be applied to images on sagittal planes as shown in FIG. 16 and 17 and can also be applied to images on coronal planes as shown in FIGS. 18 and 19 in the same manner as described above.

Figures 20, 21:
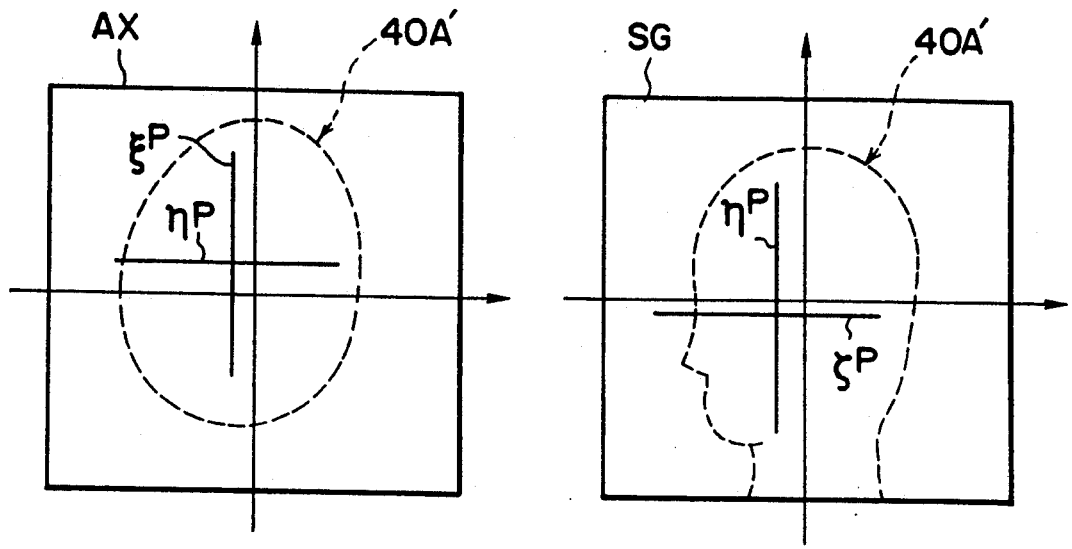
FIG. 20 is a view showing a case wherein coordinate calibration is performed by applying the present invention to phantom images.
FIG. 21 is a view showing a case wherein coordinate calibration is performed by applying the present invention to images on a sagittal plane.
Figure 22:
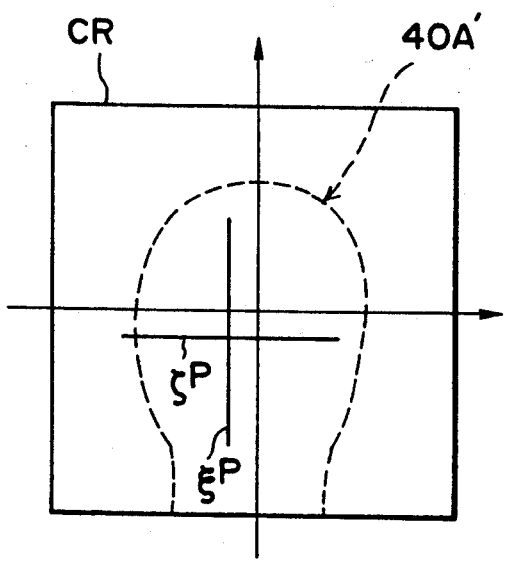
FIG. 22 is a view showing a case wherein coordinate calibration is performed by applying the present invention to images on a coronal plane.

In addition, a phantom image and a plurality of subject images may be used. For example, FIGS. 20 to 22 show a case wherein the present invention is applied to a phantom image, an image on a sagittal plane, and an image on a coronal plane.

Further, the transformation formula $\phi$ can be changed to a three-dimensional transformation formula $\phi'$ by performing calibration in three directions, and then more accurate position data can be acquired by solving the three-dimensional transformation formula $\phi'$.

In the above-described case, each indicator phantom and the frame coordinate phantom need not have three-axis coordinate display members but may have two-axis coordinate display members capable of specifying positions.

FIGS. 23A and 23B are perspective views showing a coordinate calculation apparatus according to the second embodiment of the present invention, which includes indicator phantoms 21 and a fixed type frame coordinate phantom 30.

FIG. 23A shows a state wherein phantom images are photographed. FIG. 23B shows a state wherein a subject image is to be photographed.

In the first embodiment, the frame coordinate phantom 30 is detachably mounted on the single frame 20. In contrast to this, in the second embodiment, in addition to a frame 20 to which the frame coordinate phantom 30 is fixed, another frame 20' including the indicator phantoms 21 is used. This frame 20' has geometrically the same shape as that of the frame 20. A subject image is photographed by using this frame 20', whereas phantom images are photographed by using the frame 20. That is, phantom and subject images are photographed by using the different frames 20 and 20'.

Figure 24A:
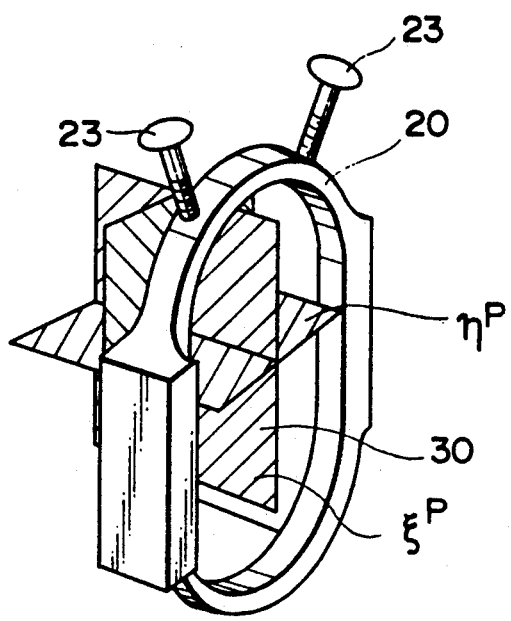
Figure 24B:
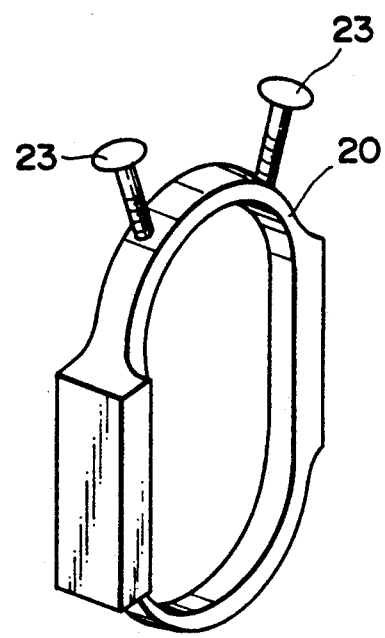

FIG. 24A and 24B are perspective views showing a coordinate calculation apparatus according to the third embodiment of the present invention, which does not include the indicator phantoms 21 but includes a detachable frame coordinate phantom 30.

FIG. 24A shows a state wherein phantom images are to be photographed. FIG. 24B shows a case wherein a subject image is to be photographed. That is, phantom and subject images are photographed by using the same frame 20.

The apparatus of the third embodiment is identical to the apparatus of the first embodiment from which the indicator phantoms 21 are omitted.

Figure 25A:
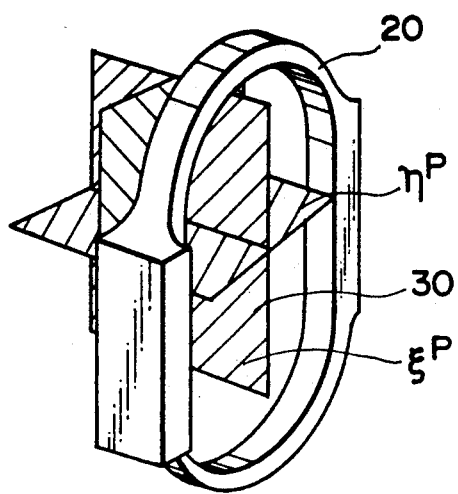
Figure 25B:
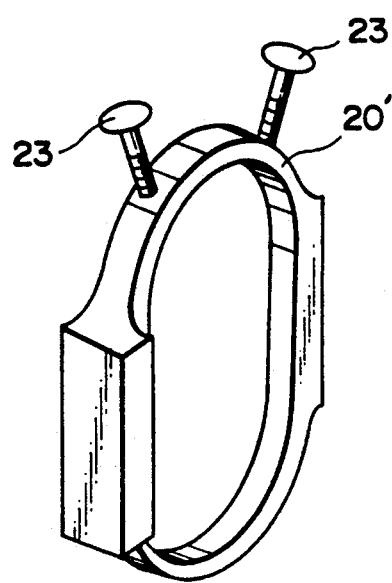

FIGS. 25A and 25B are perspective views showing a coordinate calculation apparatus according to the fourth embodiment of the present invention, which does not include the indicator phantoms 21 but includes a fixed type frame coordinate phantom 30.

FIG. 25A shows a state wherein phantom images are to be photographed. FIG. 25B shows a state wherein a subject image is to be photographed.

The apparatus of the fourth embodiment is identical to the apparatus of the second embodiment from which the indicator phantoms 21 are omitted. That is, phantom and subject images are photographed by using different frames 20 and 20'.

Figure 26:
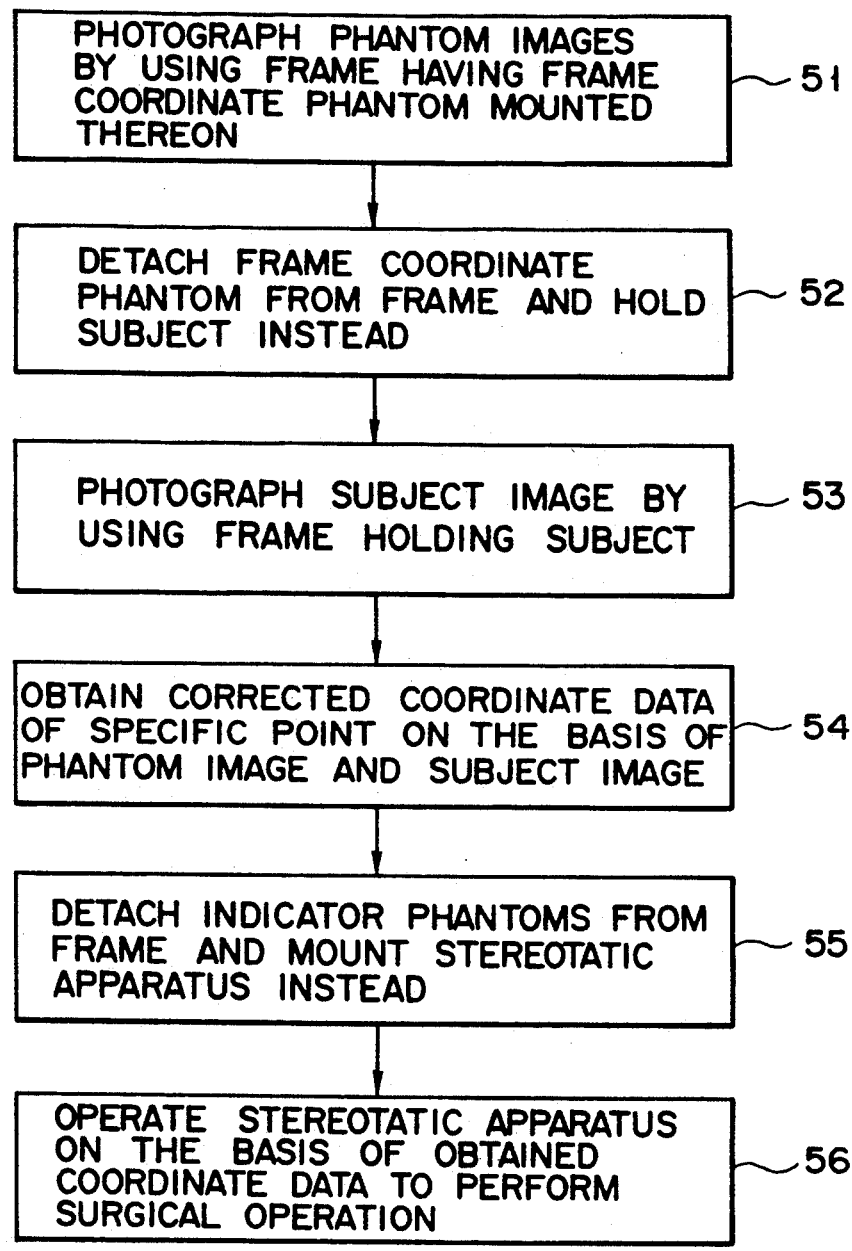
FIG. 26 is a flow chart showing a method of performing coordinate calibration and stereotaxy by using the coordinate calculation apparatuses in FIGS. 9A and 9B and FIGS. 24A and 24B.

FIG. 26 is a flow chart showing a routine constituted by steps 51, 52, 53, 54, 55, and 56, which shows a method of performing coordinate calibration and stereotaxy by using the coordinate calculation apparatuses shown in FIGS. 9A and 9B and FIGS. 24A and 24B. This routine is applied to a case wherein phantom and subject images are photographed by using the same frame 20. In this case, step 51 includes a procedure for controlling of a reference frequency corresponding a static field intensity of changing with passage of time in the MRI apparatus, thereby to improve the precision. A reference frequency (i.e., Larmor frequency) is adjusted in accordance with the intensity of the static magnetic field which changes with time. This is a socalled "magnetic field-locking control," in which the Larmor frequency $\omega$ is adjusted so as to satisfy Larmor equation $\omega = H_O$, where $H_O$ is the intensity of the static field which slightly changes with time, and $\omega$ is Larmor frequency $\omega$ preset on hardware. In addition, photography conditions in step 51 are the same as those in step 52. This also contributes to improvement in precision. In this case, photography conditions in the MRI apparatus are conditions including a pulse sequence and influencing the quality of a generated image.

Figure 27:
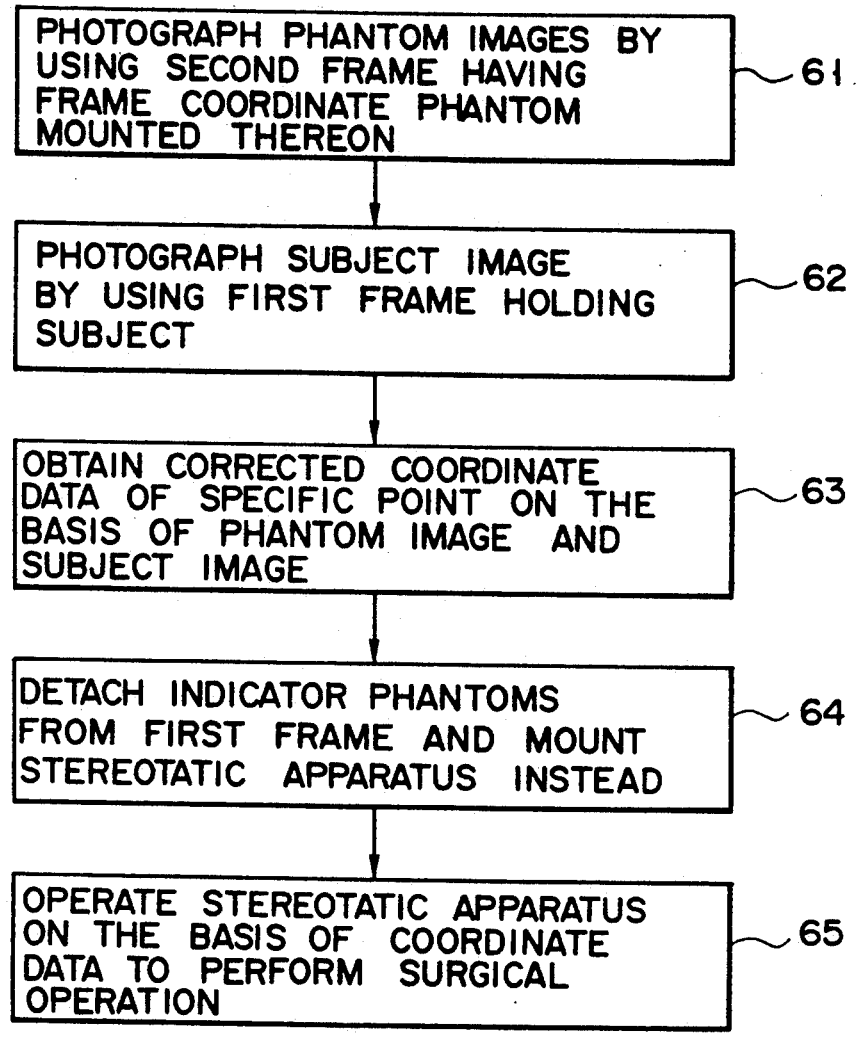
FIG. 27 is a flow chart showing a method of performing coordinate calibration and stereotaxy by using the coordinate calculation apparatuses in FIGS. 23A and 23B and FIGS. 25A and 25B.

FIG. 27 is a flow chart showing a routine constituted by steps 61, 62, 63, 64, and 65, which shows a method of performing coordinate calibration and stereotaxy by using the coordinate calculation apparatuses shown in FIGS. 23A and 23B and FIGS. 25A and 25B. This routine is applied to a case wherein phantom and subject images are photographed by using the different frames 20 and 20'. In this case, step 61 includes a procedure for controlling of a reference frequency corresponding a static field intensity of changing with passage of time in the MRI apparatus. This procedure is designed to improve the precision. In addition, photography conditions in step 61 are the same as those in step 62. This also contributes to improvement in precision.

In addition, one phantom image can be stored in the memory 114 of the computer system 111. This saves photographing a phantom image for each subject to be examined.

As has been described above, according to the apparatus and method of the present invention, image distortion caused in an MRI apparatus can be compensated, and high-precision stereotaxy can be executed.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An apparatus for calculating coordinate data of a desired point in a subject comprising:
    a frame for detachably holding the subject therein;
    an indicator phantom affixed outside said frame;
    a frame coordinate phantom being detachably mounted within said frame in place of said subject;
    magnetic resonance imaging means for imaging said frame with said subject and said indicator phantom to produce a first image, and for imaging said frame with said frame coordinate phantom and said indicator phantom to produce a second image; and
    calculating means for calculating the coordinate data of the desired point in the subject based upon said first image and said second image.

2. The apparatus of claim 1 wherein said frame coordinate phantom has marking means to display at least one axis of X, Y and Z.

3. The apparatus of claim 1 wherein said indicator phantom comprises marking means to display the coordinates of at least one axis of X, Y and Z coordinates in said first and second images.

4. The apparatus of claim 1 wherein said calculating means further comprising means for locating an image of said indicator phantom in said first image and an image of said indicator phantom in said second image, for obtaining a transformation formula between said image of said first indicator phantom in said first and second images, and for calculating a position in said subject based upon said transformation formula and a position in said frame coordinate phantom.

5. An apparatus for calculating coordinate data of a desired point in a subject comprising:
    a first frame for holding the subject therein;
    a first indicator phantom affixed outside said first frame;
    a second frame having geometrically the same shape as that of said first frame;
    a second indicator phantom affixed outside said second frame;
    a frame coordinate phantom affixed inside said second frame;
    magnetic resonance imaging means for imaging by magnetic resonance said first frame with said subject and said first indicator phantom to produce a first image, and for imaging said second frame with said frame coordinate phantom and said second indicator phantom to produce a second image; and
    calculating means for calculating the coordinate data of the desired point in the subject based upon said first image and said second image.

6. The apparatus of claim 5 wherein said frame coordinate phantom has marking means to display at least one axis of X, Y and Z.

7. The apparatus of claim 5 wherein said first and second indicator phantoms each comprises marking means to display the coordinates of at least one axis of X, Y and Z coordinates in said first and second images.

8. The apparatus of claim 5 wherein said calculating means further comprising means for locating an image of said first indicator phantom and said second indicator phantom, for obtaining a transformation formula between said image of said first indicator phantom and said second indicator phantom, and for calculating a position in said subject based upon said transformation formula and a position in said frame coordinate phantom.

* * * * *